United States Patent [19]

Erdman

[11] 4,020,949

[45] May 3, 1977

[54] BOTTLE INSPECTION DEVICE

[75] Inventor: Frank H. Erdman, Bradenton, Fla.

[73] Assignee: Tropicana Products, Inc., Bradenton, Fla.

[22] Filed: Aug. 18, 1975

[21] Appl. No.: 605,466

[52] U.S. Cl. .............................. 209/73; 209/74 M; 209/111.7 R; 250/223 B; 356/240
[51] Int. Cl.² ........................................ B07C 5/344
[58] Field of Search ............. 209/73, 111.7, 111.6, 209/74 M; 250/223 B; 74/3.5; 356/240

[56] References Cited
UNITED STATES PATENTS

| | | | |
|---|---|---|---|
| 2,542,090 | 2/1951 | Lorenz | 209/74 M |
| 2,985,008 | 5/1961 | Renard | 209/74 R X |
| 3,245,533 | 4/1966 | Rottmann | 209/111.7 |
| 3,328,000 | 6/1967 | Rottmann | 356/240 |
| 3,479,514 | 11/1969 | Kidwell | 356/240 X |
| 3,687,285 | 8/1972 | Messervey | 209/74 R |
| 3,687,559 | 8/1972 | Fischer | 250/223 B |
| 3,923,158 | 12/1975 | Fornaa | 209/111.7 T |

*Primary Examiner*—Allen N. Knowles
*Attorney, Agent, or Firm*—Burns, Doane, Swecker & Mathis

[57] ABSTRACT

A bottle check detector is disclosed which detects both vertical and horizontal checks in the neck portion of a transparent glass bottle that may be of a rectangular half-gallon size, a circular half-gallon size, a round quart size or a square quart size. The check detector includes a continuously rotating head having infrared light emitters and receivers for detecting a wide range of horizontal and vertical checks. The emitters and receivers are pulsed and coupled to detect any checks. The head also includes downwardly extending fingers having reflecting surfaces thereon positioned below the plane of the bottle mouth to reflect the light reflected by generally vertical cracks upwardly to light receivers. Bottles are singularly advanced into an inspection position directly below the rotating head by an intermittently advancing conveyor having opposed lugs to space bottles from one another and to push them forwardly. The intermittently advancing conveyor is synchronously driven with the continuously rotating head with a geneva gear means. A mechanical memory device is provided to actuate a bottle segregation device spaced from the inspection station.

22 Claims, 14 Drawing Figures

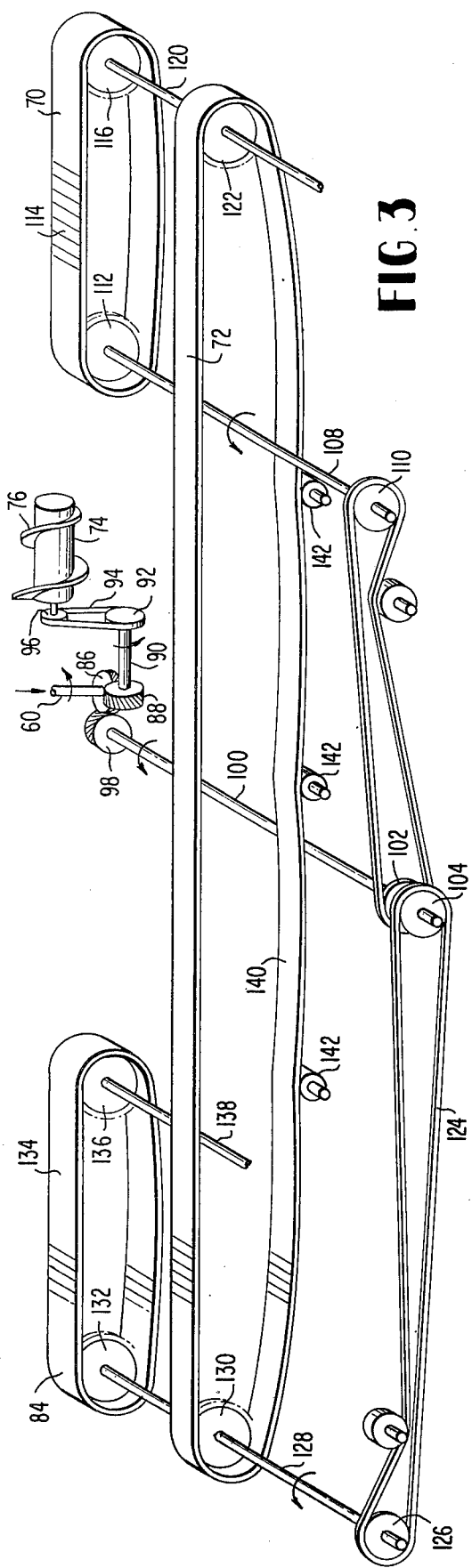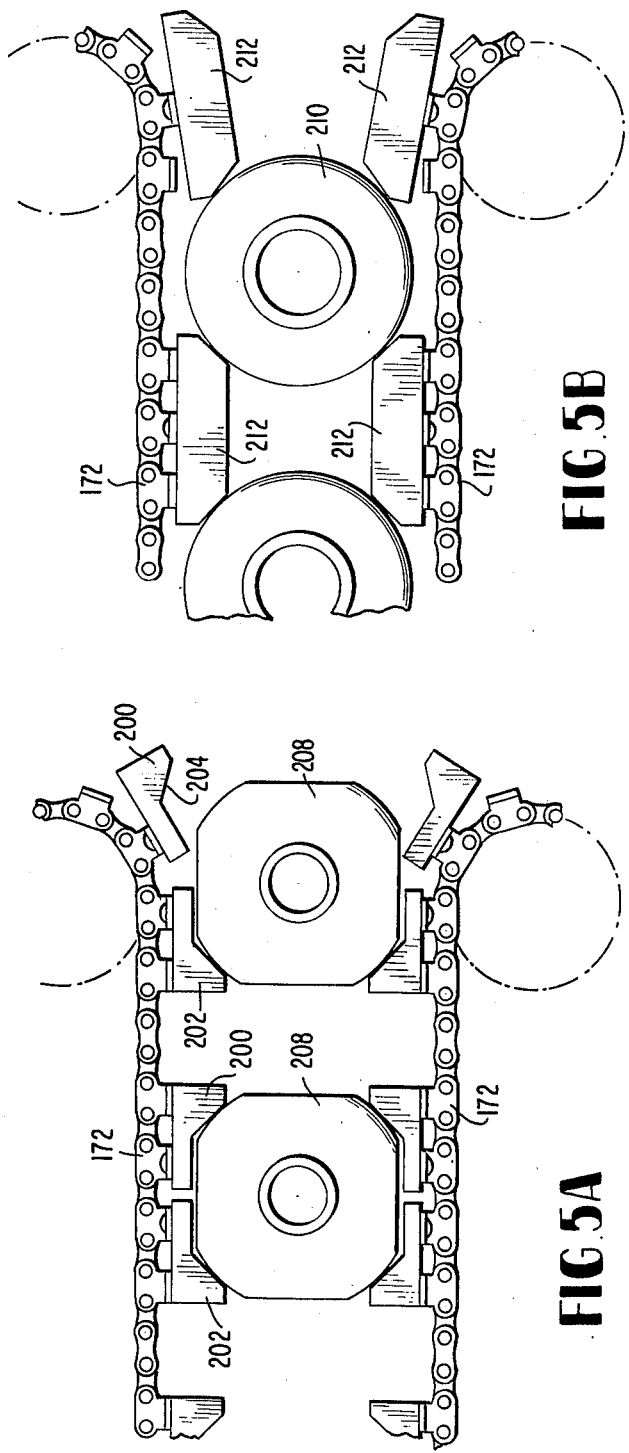

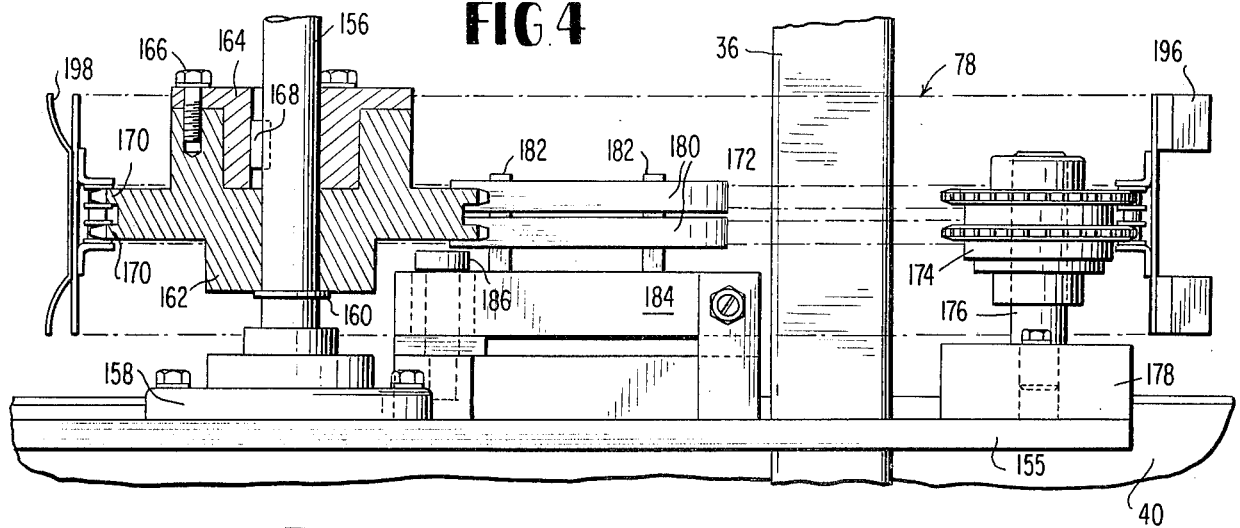
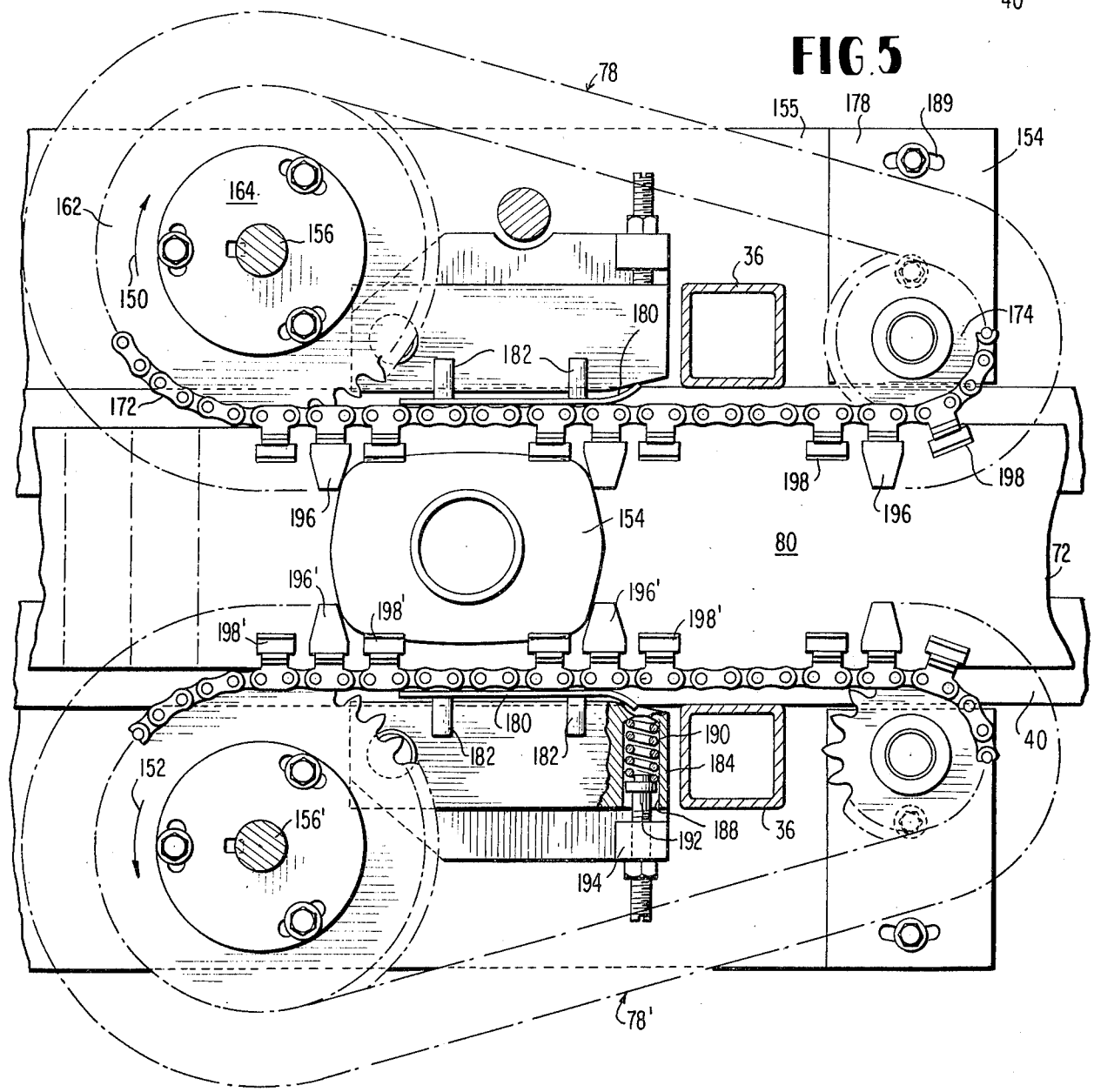

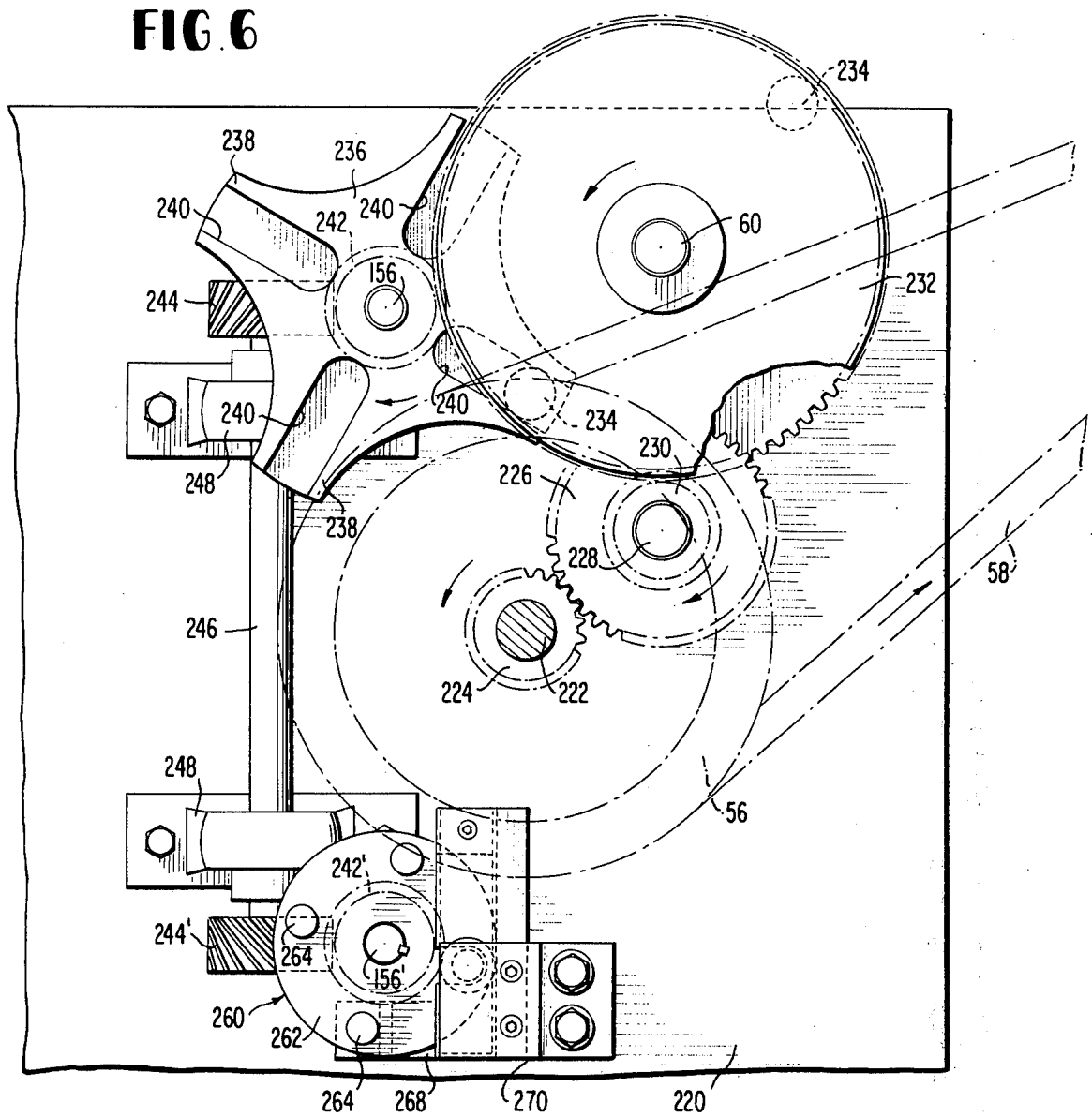
FIG. 6
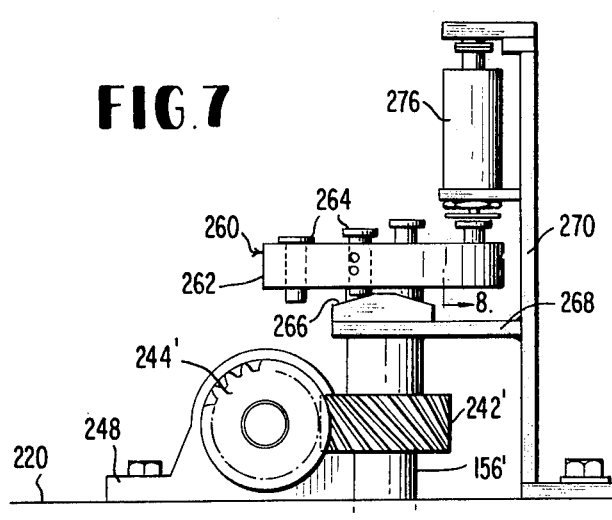
FIG. 7
FIG. 8

BOTTLE INSPECTION DEVICE

BACKGROUND OF THE INVENTION

This invention relates generally to the detection of flaws, checks and like imperfections, in the neck portion of a bottle. More specifically, the invention concerns bottle inspecting apparatus for detection of a wide range of both horizontal and vertical imperfections in the neck portion of a bottle by a continuously rotating sensing head.

In the past, there has been a need to inspect the neck and threaded mouth portions of glass bottles to be used as a container for foodstuffs and the like. The existence of checks, cracks and imperfections has been the cause of failure of the bottle or the bottle neck portion when the bottles are subsequently filled with a liquid for distribution in the channels of commerce. Typically, the loss or failure of a bottle constitutes a loss of the contents therefo as well as well as establishing an injury potential for consumers, employees and the like.

One characteristic of bottle imperfections which has been utilized in the past for bottle inspection devices is the tendency of the imperfections to reflect incident light. Accordingly, some previously known bottle check detectors have detected reflected light as an indication of the presence of bottle checks.

Many bottle inspecting devices heretofore known have employed some means for rotating individual bottles below a stationary inspecting head to optically indicate the presence or absence of imperfections. Such known devices, however, are not well adapted to handle bottles of various volumetric capacity and cross-sectional configuration: e.g., half-gallon and quart sizes; round, rectangular and square bottles. In addition, the rotation of the bottle beneath an inspecting head does not lend itself to the high speed inspection of bottles, i.e., a rate of a hundred bottles or more per minute.

Other known bottle inspection devices raise each bottle to an inspection station which rotates with respect to the bottle to perform an optical inspection. See, for example, U.S. Pat. No. 3,479,514, issued to Kidwell on Nov. 18, 1969. Such devices, however, do not inspect for both vertical and horizontal cracks with a single inspection head. Accordingly, a plurality of inspection devices are necessary to completely inspect a bottle for both types of cracks.

Still other bottle inspect devices carry bottles by a conveyor to an inspection station where they are detained by a laterally swinging arm that holds them in position below a rotating inspection head See Rottmann Pat. Nos. 3,245,533, and 3,328,000 issued on Apr. 12, 1966 and June 27, 1967 respectively. The rotating inspection heads of these known devices are adapted only to determine the presence of generally horizontal cracks and do not effectively indicate the presence of vertical cracks which are equally deleterious.

Ordinally, no synchronization is used between bottle detaining mechanisms and rotating inspection heads in the known devices, thereby making destructive contact possible between the rotating head and bottles being positioned for inspection. Other difficulties with the known rotating head devices include the slowness in the inspection process and a single pass inspection. Speed of inspection is important since it permits fewer inspection stations to examine a given number of bottles in a given period of time. A multi-pass inspection is desirable to insure that randomly placed imperfections near the beginning or end of the inspection cycle are detected. Devices are also known which utilize a rotating head to inspect the surface of a bottle continuously moving therebelow. See, for example, the Calhoun et al patent 3,349,906, issued Oct. 31, 1967. These devices, however, are not adapted to determine the presence or absence of imperfections in the bottle material itself and are also subject to error induced by spurious reflections from bottles being advanced into the inspection position below the rotating head.

Thus, the need continues to exist for a high speed bottle inspection device which is capable of rapidly and effectively determining the presence of bottle imperfections which may be in both generally horizontal and generally vertical planes.

OBJECTS AND SUMMARY OF THE INVENTION

It is, therefore, a general object of the present invention to provide a novel bottle check inspecting apparatus that overcomes problems of the type noted above.

It is a more particular object of the present invention to provide a novel, high speed bottle check inspection apparatus which may handle bottles at a rate exceeding 100 bottles per minute.

It is a further object of the present invention to provide a novel bottle check inspection apparatus which inspects for both generally vertical and generally horizontal cracks, checks and imperfections in bottle neck portions.

It is a still further object of the present invention to provide a novel bottle check inspection apparatus having a continuously rotating head which is synchronously related to a bottle advancing mechanism that advances bottles intermittently into an inspection position below the rotating head.

It is still another object of the present invention to provide a novel bottle check inspection apparatus having a mechanical memory device which delays actuation of a bottle separating device until imperfect bottles are in position for separation from perfect bottles.

A yet still further object of the present invention is to provide a novel method of inspecting glass bottles for both horizontal and vertical cracks, checks, imperfections and the like by the use of the rotating head.

These and many other objects of the present invention will be apparent to those skilled in the art from this specification and the claims appended hereto.

Bottle check inspection apparatus according to a preferred embodiment of the present invention which is intended to substantially accomplish the objects as set forth above includes: an inspection station having an inspection position; imperfection sensing means positioned above inspection position, operable to generate a reject signal when horizontal and vertical imperfections are detected, and operable for continuous rotation; conveyor means operable to advance bottles towards the inspection station and to move inspected bottles toward a further processing station; intermittent advancing means located at the inspection station, synchronously operable with the sensing means and operable to receive bottles from the conveyor means and intermittently advance bottles one at a time to the inspection station below the sensing means; and ejection means positioned adjacent the intermittent advancing means and operable to receive the reject signal and segregate an imperfect bottle from perfect bottles.

BRIEF DESCRIPTION OF THE DRAWINGS

This invention will be best understood by reference to the figures accompanying this specification wherein like reference numerals have been applied to like elements and wherein:

FIG. 3 is a perspective drawing illustrating the drive for elements of a table portion;

FIG. 4 is a view in partial cross section illustrating the mechanical drive and support for bottle advancing conveyors;

FIG. 5 is a plan view of the bottle advancing conveyors with a bottle illustrated in place;

FIGS. 5A and 5B illustrate alternate embodiments for opposing lugs carried by the advancing conveyors to accommodate bottles of different cross sections and volumetric capacity;

FIG. 6 is a plan view illustrating means for driving an inspection head and converting continuous rotary motion to intermittent rotary motion to drive the advancing conveyors;

FIG. 7 is an elevation of a mechanical memory device according to the present invention;

FIG. 8 is an elevation in partial cross section taken along the line 8—8 of FIG. 7;

DESCRIPTION OF THE PREFERRED EMBODIMENT

Figure 1:
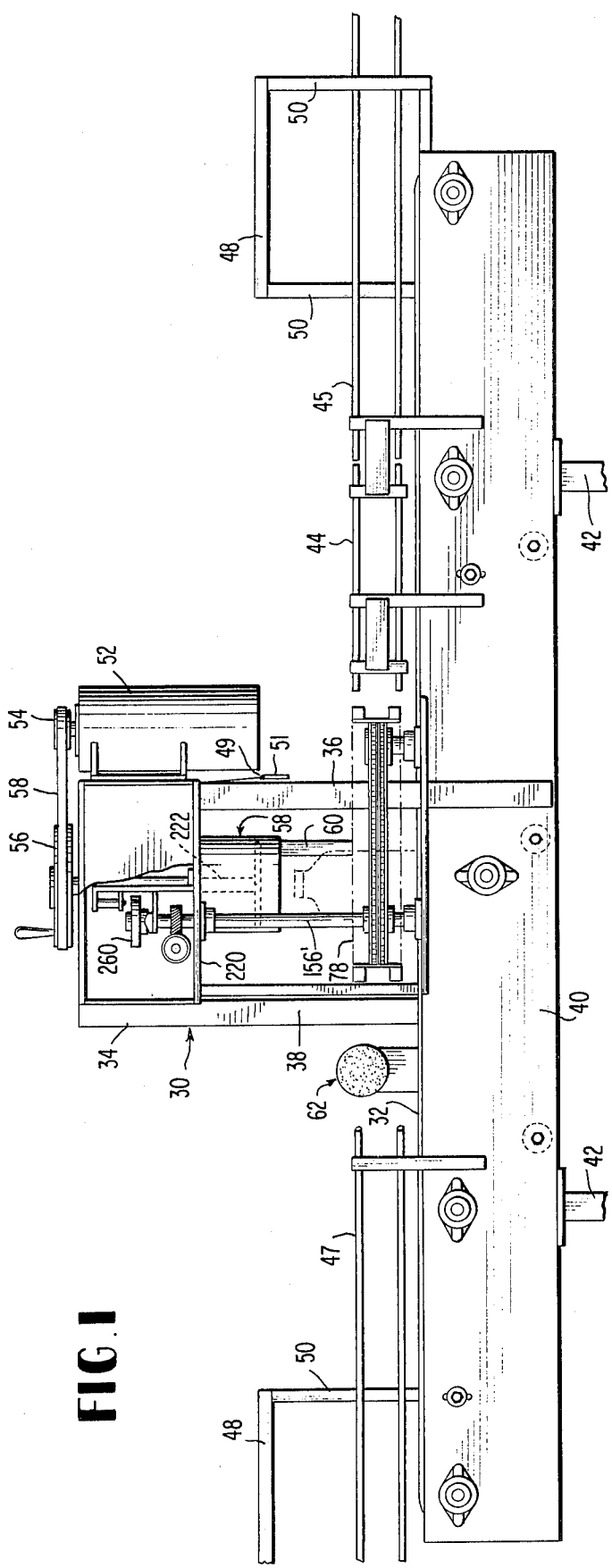
FIG. 1 is a side elevation of station, check detecting apparatus according to a preferred embodiment of the invention with a portion broken away.

Turning now to FIG. 1, a bottle check detecting apparatus 30 includes a table portion or bed 32 on which bottles are translated from right to left. Typical bottles are transparent glass bottles having generally uniform cross section and volumetric capacity. The apparatus 30 includes an inspection tower 34 which is supported above the generally horizontal bed 32 by a pair of columns 36 and a pair of brackets 38. In FIG. 1 only one of the columns 36 and the brackets 38 is illustrated. The second column 36 and the second bracket 38 are disposed behind the two illustrated as will become more apparent from other figures.

Extending downwardly from the bed 32 is a supporting frame 40. The frame 40 may by supported vertically relative to a floor or other generally horizontal surface by a plurality of legs 42 which may be arranged as required.

Extending vertically upwardly from the frame 40 are fences 44, 45, 47 which serve to guide bottles passing from right to left through an inspection station 80 positioned below the inspection tower 34. Each fence 44, 45, 47 may include vertical supports with laterally extending guides therebetween. The fences are spaced from one another to allow bottles to pass therebetween in guided relation. At each end of the bottle inspection apparatus 30 (FIG. 1) a suitable generally horizontal bar 48 and supporting posts 50 are provided to support the fences 45, 47.

Positioned centrally between the columns 36 and attached to the tower 34 is a bracket 49 that pivotally supports a plate 51 from its upper edge. The lower edge of the plate 51 is positioned at a vertical distance above the bed 32 corresponding to the height of the highest bottle which can be accommodated. In the event that an intolerably high bottle should elude earlier detection, it will trip the plate 51 by engaging its lower edge and cause the apparatus 30 to stop. A suitable conventional limit switch may be used to effect the stoppage. After the high bottle is removed, the apparatus 30 will function normally until another high bottle is encountered.

The inspection tower 34 has a variable speed motor 52 mounted thereon to provide the necessary rotary motion to drive the bottle inspection apparatus 30. As will become apparent, the motor 52 provides all the power for the inspection apparatus 30. The motor 52 is provided with a drive pulley 54 which is operably connected with a main drive pulley 56 of the inspection apparatus 30. The drive pulley 54 and the main drive pulley 56 may be operatively connected by a V-belt 58, a chain or other suitable power transmitting device. Preferably, a suitable conventional friction clutch is interposed between the shaft of the motor 52 and the drive pulley 54. In this manner, the motor 52 will not cause a bottle to be crushed if it becomes jammed beneath the inspection tower 34.

The main drive pulley 56 is operatively connected to continuously drive a rotating sensing or inspection head 58. The inspection head is disposed directly above an inspection position 82 in the inspection station below the inspection tower 34. In addition, the main drive pulley 56 is operatively connected to a table drive shaft 60 which extends downwardly from the inspection tower 34 to the bed 32 and the frame 40.

Positioned adjacent to the inspection tower and carried above the bed 32 is a bottle ejecting or segregating apparatus 62. The ejecting apparatus 62 may include an electrically operated solenoid 63 that responds to a reject signal generated by the inspection head 50 causing a pad 65 to traverse the bed 32 and to exclude imperfect bottles from continued movement along the longitudinal length of the bed 32 and to subsequent processing apparatus such as filling machines or the like.

Figure 2:
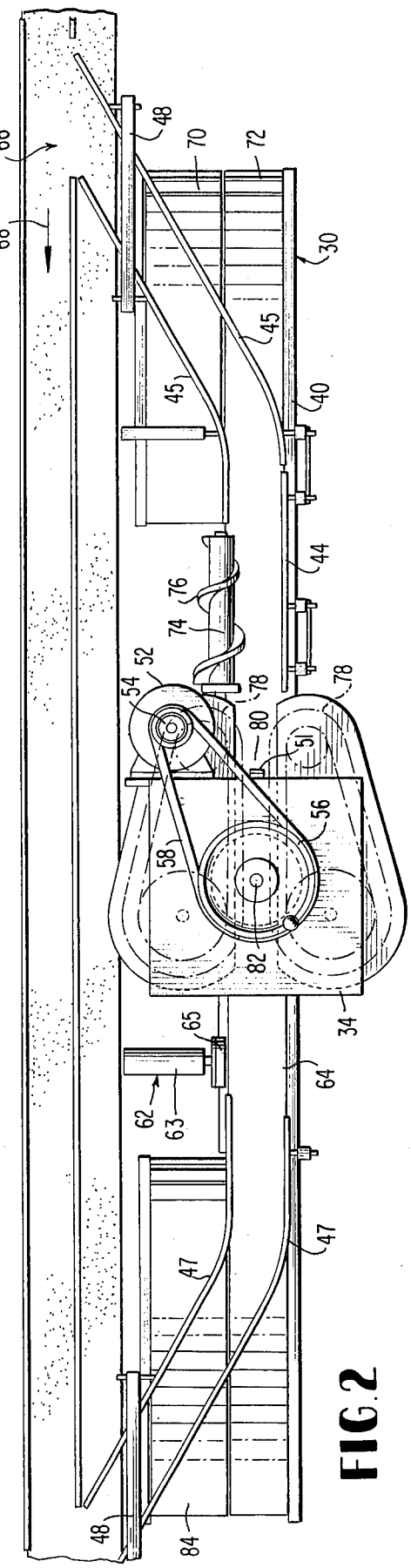
FIG. 2 is a plan view of the bottle check detection apparatus of FIG. 1.

Turning now to FIG. 2 a space 64 is provided in the fence 44 in general alignment with the ejecting apparatus 62 and adjacent to the inspection tower 34. Imperfect bottles are removed from the flow of perfect bottles through this space 64 when the pad 65 extends across the bed 32 and pushes an imperfect bottle before it. Perfect bottles are permitted to proceed without interruption by the ejecting apparatus 62.

A continuous supply of glass containers or bottles may be furnished along the conveyor 66 in the direction of arrow 68 (FIG. 2). The bottles are diverted laterally by the inclined fences 45 from the direction of movement of arrow 68 and into the bottle inspection apparatus 30.

To move the bottles laterally from the supply conveyor 66 and into the inspection apparatus 30, a short feeding conveyor 70 is provided that is supported by the frame 40. The feeding conveyor 70 is transversely disposed with respect to the inclined fences 45 such that an acute angle less than 45° is defined therebetween. Bottles are moved laterally as the feeding conveyor 70 carries the bottle against one fence 45 that causes the bottles to slide transversely of the feeding conveyor 70 and toward a longitudinal conveyor 72.

The longitudinal conveyor 72 is immediately adjacent to the feeding conveyor 70, extends substantially along the entire length of the bottle inspection apparatus 30 and is supported on the frame 40 with its upper moving surface on the bed 32. As the bottles move from the supply conveyor 70 and along the longitudinal conveyor 72 between the fences 44, they are engaged by a rotationally driven bottle spacer or feed screw 74. The bottle spacer 74 is positioned at one side of the longitudinal conveyor 72 immediately adjacent to the inspection tower 34 and includes a generally helical screw flight 76. The radial height of the screw flight 76 increases in the direction of bottle advancement along the longitudinal conveyor 72. In this manner, the screw flight 76 extends into the path of the supply of bottles and spaces the bottles from one another so that they may be advanced into proper engagement with intermittently advancing opposed conveyor assemblies 78 of the inspection tower 34.

The intermittently advancing conveyor assemblies 78 will be described more fully hereinafter. For the present discussion the intermittently advancing conveyor assemblies 78 are positioned on each side of the longitudinal conveyor 72, cooperate to define a bottle inspection station 80 therebetween and are synchronously driven from the main drive pulley 56. Bottles are advanced through the inspection station 80 by the intermittently advancing conveyor 78 which alternately advances and retards movement of the bottles with respect to the continuously moving longitudinal conveyor 72. More particularly, the bottles advance at a rate up to 3 times the linear speed of the longitudinal conveyor 72 and then dwell at a location while the longitudinal conveyor 72 slips forwardly beneath the bottles.

The intermittently advancing conveyor assemblies 78 advance the bottles through the inspection station 80 to the inspection position 82 which is located directly below the rotating head 58 (see FIG. 1) and then release the bottles for further movement by the longitudinal conveyor 72.

As the bottles leave the inspection tower 34, they are advanced by the longitudinal conveyor 72 until they engage the inclinded fences 47. The inclined fences 47 direct the bottles laterally and toward the bottle supply conveyor 66.

The bottles first enter a return conveyor 84 carried by the frame 40 with its upper surface coplanar with the upper moving surface of the longitudinal conveyor 72. The return conveyor is positioned such that an acute angle less than 45° is defined with the inclined fences 47. The return conveyor 84 and the inclined fences 47 cam bottles from the longitudinal conveyor 72 across the return conveyor 84 and back towards the bottle supply conveyor 66.

Turning now to FIG. 3, the details of the conveyor drive system will be described in more detail. As noted above, power from the variable speed motor 52 is conveyed to the frame 40 by the table drive shaft 60. The lower end of the table drive shaft 60 is provided with a drive gear 86. The drive gear 86 may be provided with suitable conventional helical drive gear surfaces.

The drive gear 86 drives a first driven gear 88 having helical gear surfaces meshed with those of the driving gear 86. The first driven gear 88 rotates a lay shaft 90 having a sprocket 92 at one end which sprocket 92 is adapted to drive a chain 94. The chain 94 drives a second sprocket 96 which is carried by one end of the bottle spacing screw 74 described above.

A second driven gear 98 has helical gear surfaces and meshes with the driving gear 86 to provide rotary motion for driving the feeding conveyor 70, the longitudinal conveyor 72 and the return conveyor 84 described above. The driven gear 98 is carried at one end of a cross shaft 100 which is provided with first and second drive sprockets 102, 104, respectively, of equal diameter.

The first drive sprocket 102 engages a drive chain 106 which imparts rotary motion to a first drive shaft 108 through a driven sprocket 110 carried adjacent an end thereof. The first drive shaft 108 carries a driving roller 112 which drivingly engages the inner surface of the feeding conveyor 70. The feeding conveyor 70 may be an endless belt as illustrated and may be fabricated of suitable conventional materials. The belt 70 has an upper surface 114 which is supported at one end by the driving roller 112 and at its other end by an idling roller 16.

The idling roller 116 is carried on a shaft 120 which includes a second idling roller 122 that is axially spaced along the shaft 120 from the idler roller 116 and has an equal diameter. The idler roller 122 provides a support for one end of the longitudinal conveyor belt 72 which also may be fabricated from suitable conventional materials. With the idler rollers 116, 112 both carried by the same shaft 120 and having equal diameters, it will be apparent that the feeding conveyor 70 and the longitudinal conveyor 72 have the same surface speed.

The second drive sprocket 104 drives another chain 124 which cooperates with another driven sprocket 126 to drive a second drive shaft 128. The second drive shaft 128 includes a pair of axially spaced drive rollers 130, 132 having equal diameters.

The first drive roller 130 is disposed at one end of the longitudinal conveyor 72 and drivingly engages the inner surface of the longitudinal conveyor 72 to drive the endless belt in longitudinal direction along the bed 32.

The second driving roller 132 engages the inner surface of the return conveyor 84 and supports one end of its upper surface 134. The second end of the upper surface 134 is supported by an idle roller 136 carried by an idling shaft 138.

The cross shaft 100, the first drive shaft 108, the second drivd shaft 128, the first idling shaft 120, and the second idling shat 138 are suitably supported by the frame 40 (FIG. 1) below the plane of the bed 32.

The lower run 140 of the longitudinal conveyor 72 is supported by one or more idling rollers 142 as desired. It will now be apparent that, by virtue of the common diameter of the rollers 130, 132 carried by the shaft 128, the upper moving surfaces of the longitudinal conveyor 72 and the return conveyor 84 have the same speed. Elementary trigonometric considerations will demonstrate that the bottles are spaced further apart along the longitudinal conveyor 72 than they are spaced when traversing the feeding conveyor 70 and the return conveyor 84.

Returning now to the advancing conveyor asseblies 78, each of the intermittently driven advancing conveyors 78 has identical constituent parts with the exception of the fact that they are mirror images of one another along the center line of the longitudinal conveyor 72. Accordingly, it will suffice to describe in more detail only one of the advancing assemblies 78. The second advancing assembly 78 has corresponding parts correspondingly located and designated with a prime (') where necessary.

Turning briefly to FIG. 5, the sole difference between the two advancing assemblies 78 is that they are driven in opposite directions as illustrated by the arrows 150, 152, such that a bottle 154 may be advanced through a bottle receiving space in the longitudinal direction traversed by the longitudinal conveyor 72.

Turning now to FIG. 4, each intermittently driven advancing conveyor assembly 78 is supported laterally with respect to the frame 40 by an outwardly extending shelf 155. Intermittent rotary motion is imparted to the assembly 78 through an intermittently driven generally vertical shaft 156. The shaft 156 is supported at its lower end by a suitable bearing assembly 158 carried on the shelf 155. The drive shaft 156 may be provided with a generally radially outwardly extending flange 160 against which a drive sprocket 162 rests in vertical abutment. The drive sprocket 162 has a collar 164 fastened thereto by bolts 166. The collar 164 is adapted to receive a key 168 carried by the shaft 156 to prevent relative rotation therebetween. The drive sprocket 162 is provided with parallel rows of teeth 170 which comprise a drive for one end of an endless double chain belt 172.

Turning now to FIG. 5, the drive sprocket 162 operates to translate the chain belt 172 longitudinally in the direction of the motion of longitudinal conveyor 72. The endless chain belt 172 is supported at its opposite end by an idle sprocket 174. Returning to FIG. 4, the idler sprocket 174 is carried by a vertical shaft 176 supported by an adjustable block 178 supported by the shelf 155. As may be seen from FIG. 5, the adjustable block 178 is provided with an arcuate groove 189 permitting the block 178 to be moved with respect to the shelf 155 to adjust the tension in the double chain belt 172.

Between the drive sprocket 162 and the idling sprocket 174 and adjacent to the inspection station 80, a pair of chain guide shoes 180 may be provided. The guide shoes 180 (see FIG. 4) are positioned in alignment with the chain 172 and are mounted on spaced apart vertical posts 182. The posts 182 are supported by a bar 184 that is pivotally mounted to a pin 186 connected to the shelf 155.

The bar 184 is provided with a lateral bore 188 adjacent one end thereof (see FIG. 5) which is adapted to receive a spring 190. The spring 190 is retained in the bore 188 by an axial adjustable plunger 192 mounted on a vertically extending block 194. The plunger 192 and spring 190 cooperate with the bar to resliently push the shoes 180 toward the inspection station 80 defined between the two opposed advancing assemblies 78.

In order to accommodate bottles of rectangular half gallon capcity, each of the double chain belts 172 (see FIG. 5) is provided with bottle engaging apparatus such as outwardly projecting spacer lugs 196. The spacer lugs 196 are arranged in opposed paired relationship transversely with respect to the longitudinal conveyor 72 and transversely with respect to the bottle inspection station 80. Along each side of the spacer lugs 196 are generally resilient fingers 198. The resilient fingers 198 project outwardly (see FIG. 4) above and below the chain belt 172 to engage bottles at both high and low location. The fingers 198 have sufficient resilience to support a bottle vertically without a horizontal support. In this fashion, undulations of the longitudinal conveyor 72 passing below the bottle do not vibrate the bottle during inspection. At most, the undulations can slightly elevate the bottle to a higher position where it is still held by the fingers 198. The spacer lugs 196, on the other hand, also project outwardly from the chain belt 172 and may comprise blocks of suitable nonabrasive hard high molecular weight polymeric material intended not to damage the glass bottles being inspected. One suitable material is "Nylatron" which has a high molecular weight matrix with a molybdenum disulphide filler. It is the spacer lugs 196 which alternately retard and push the bottles relative to the longitudinal conveyor 72 as described above.

When one pair of lugs 196, 196' are in alignment with the shafts 156, 156' and the adjacent pair of lugs are supported by the shoes 180, a bottle 154 disposed therebetween (i.e. forwardly advanced from the position actually shown in FIG. 5) is in the inspection position 82. In addition, the cooperation between the two pair of opposed lugs 196, 196' and the resilient fingers 198, 198' therebetween assures that the bottle 154 is held securely during inspection.

An important feature of the present invention is the ability of the bottle inspection apparatus to accommodate glass bottles having different shapes and capacities without major modification. In this connecton, as illustrated in FIG. 5, the lugs 196, 198 are adapted to receive glass bottles 154 of the rectangular half gallon variety. To accommodate bottles of the square quart size (see FIG. 5A) the chain belt 172 may only be provided with a different set of lugs. For example, as depicted, each chain belt 172 is provided with lugs 200, 202 which cooperate to define an articulated recess which closes in behind a square quart size bottle 208 to advance the bottle 208 or retard it as required by the advancing assembly. Each lug 202 includes a relatively thin end which is connected to a link of the chain belt 172 and a relatively thick end which is cantilevered from the thin end. When the articulated lugs 200, 202 have the bottle 208 positioned therebetween, the relatively thick end of the lug 200 is supported by an adjacent link of the chain belt 172. The second lug 202 is mounted in the same fashion as the lug 200 except that the relatively thin end of the lug 202 is mounted on the chain link adjacent to that link on which the lug 200 is mounted.

When dealing with bottles of the round quart variety the lugs illustrated in FIG. 5B may be attached to the chain belt 172. The round quart bottles 210 are spaced between generally trapezoidally shaped lugs 212. Each lug 212 is attached at its center to one link of the chain belt 172 and is supported at each end by chain links adjacent to the one link to which the lug 212 is connected.

Returning briefly to FIG. 1, the means whereby the drive motor 52 provides an intermittent rotary motion to the intermittently driven shafts 156, 156' will be described in more detail. The shafts 156, 156' extend vertically downwardly from the inspection tower 34 and are supported at their upper end by conventional bearings attached to a floor 220 of the inspection tower 34. It will also be noted that the inspection head 58 is carried by a vertically extending shaft 222 which is directly connected to the main drive gear 56 of the inspecton tower 34. The shaft 222 is driven by the variably speed motor 52 such that it rotates at approximately 480 rpm. The speed of 480 rpm gives a bottle inspection rate of 2 bottles per second. Higher or lower rotary speeds may be used if desired and will proportionately increase or descrease the bottle inspection rate.

Turning now to FIG 6, the drive belt 58 causes the main drive pulley 56 to rotate in a counterclockwise direction as illustrated. The shaft 222 is provided with a spur gear 224 which is keyed thereto to prevent relative rotation therebetween. The spur gear 224 is in meshed relationship with a second spur gear 226 which is driven thereby. The second spur gear is carried by a vertical shaft 228 that also includes a third spur gear 230 which is in meshed contact with a spur gear 232 carried at the upper end of the table drive shaft 60. The spur gears 224, 226, 228 and 232 are not all coplanar and cooperate to reduce the speed of rotation from the 480 rpm of the main shaft 222 to approximately 120 rmp for the gear 232.

The gear 232 is also provided with a pair of pins 234 which extend vertically downwardly therefrom and which are spaced circumferentially from one another at 180° such that they are diametrically opposed.

Positioned in a plane vertically below that of the gear 232 is the driven gear 236 of a geneva gear set of which the gear 232 is the input gear. The gear 236 is provided with four equi-angularly spaced arms 238 that are each provided with an elongated generally radial slot 240. The slots 240 are designed such that their lateral width corresponds essentially to the diameter of the pins 234 depending from the driving spur gear 232. As the spur gear 232 rotates a pin 234 engages a slot 240 and, with continued rotation of the gear 232, causes rotation of the driven geneva gear 236 until the pin 234 radially leaves the slot and assumes the position illustrated in FIG. 6. During the time the driving geneva gear 232 rotates through an additional angle of 90° there is no motion of the driven geneva gear 36. During the driven part of each revolution, the driven geneva ger 236 may rotate with an angular velocity up to three times that of the driving gear 232 while during the next portion of each revolution there is a dwell period with no motion of the driven gear 236. The driven geneva gear 236 is fashioned to complete 120 cycles per minute with the shaft 222 operating at 480 rpm.

Accordingly, the pins 234 and the slots 240 cooperates and constitute a means for transforming continuous rotary motion of the driving gear 232 into an intermittent rotary motion which is transmitted directly to the shaft 156 on which the geneva gear 236 is mounted. It will be recalled from the discussion above that the shaft 156 provides the intermittent motion necessary for the advancing assembly 78 (see FIG. 5, for example). Moreover, the geneva gear assembly is also effective to synchronize motion of the advancing assemblies 78 with that of the rotating head 58 (see FIG. 1).

Returning now to FIG. 6, the shaft 156 is provided with a helical drive gear 242 which cooperates to drive a meshed helical gear 244. The meshed gear 244 is carried at one end of the transverse shaft 246 which is supported adjacent each end by a suitable bearing assembly 248 attached to the floor 220. At the second end of the transverse shaft 246 is another helical gear 244'. The second helical gear 244' cooperates with a helical driven gear 242' carried by the second intermittently driven shaft 156' which extends from the inspection tower 34 (ss FIG. 1) to the bottle advancing assembly 78. In this manner the shafts 156, 156' are counterrotating and synchronized to advance bottles through the inspection station 80.

The mechanical connection between the primary shaft 222 and the intermittently driven counterrotating shafts 156, 156' is such that the shaft 222 rotates through two complete revolutions during each dwell period. Thus, the inspection head 58 (see FIG. 1) attached to the shaft 222, makes two complete inspections of a bottle during the dwell period to effect a redundant inspection.

During bottle inspection, the inspection head 58 generates a reject signal if an imperfect bottle is detected. It will be seen, however, that the bottle in the inspection position below the inspection head 58 may not be ejected from the prior detection apparatus until the bottle is in general alignment with the ejecting assembly 62. Therefore, it is necessary to delay the operation of the ejection assembly 62 until the bottle is in general alignment therewith.

Accordingly, the second intermittently driven shaft 156' is provided at its upper end with a mechanical memory device 260. Turning now to FIG. 7 the mechanical memory device 260 is illustrated in greater detail and includes a generally circular disc 262 coaxial with the shaft 156' and having four slidably mounted elongated pins 264 positioned at equiangularly spaced circumferential intervals.

Spaced slightly below the lower surface of the disc 262 is an inclined cam surface 266 which is operable to reset the pins to a position extending above the disc upper surface. The cam surface 266 is carried by a generally horizontal arm 268 supported above the floor 220 by a vertical pillar 270. The cam surface 266 is in general alignment with the circular locus defined by the pins 264 as they rotate around the axis of the intermittently driven shaft 156'.

As may be seen from FIG. 8, each pin 264 includes a circumferentially extending groove 272 which may be positioned in radial alignment with either of two suitable detents 274 such as a spring biased ball. Each pair of detents 274 substantially eliminates any bouncing of the corresponding pin 264 while the disc 262 rotates. In addition each detect 274 is operable to retain the corresponding slidably mounted pin 264 in a position extending either upwardly above the upper surface of the plate 262 or downwardly below the lower surface thereof. As the plate 262 rotates any pin 264 which is extending from the lower surface is reset by the cam surface 266 to a position extending above the upper surface.

In the event that a flow, check or imperfection is detected in a bottle undergoing inspection, a pulse is generated to actuate a solenoid 276 carried by the vertical pillar 270. The solenoid 276 is spring biased upwardly by the member 278 but overcomes that spring bias upon receiving a reject signal from the continuously rotating inspection head 58. the solenoid 276 thereupon engages one of the pins 264 extending upwardly from the plate 262 and slides it downwardly so that it projects from the lower surface thereof.

The subsequent rotation of the intermittently advancing shaft 156' causes the projecting pin 264 to engage a trigger such as a limit switch 280 that signals the ejecting mechanism 62 to separate the imperfect bottle from the approved bottles. The limit switch 280 is positioned below the lower surface of the disc 262 and circumferentially positioned between the solenoid 276 and the cam surface 266. Preferably, the switch 280 is spaced at an angle between 80° and 120° from the solenoid 276 so that an imperfect bottle will in alignment with the ejection apparatus 62 when the delayed reject signal is triggered.

Figure 9:
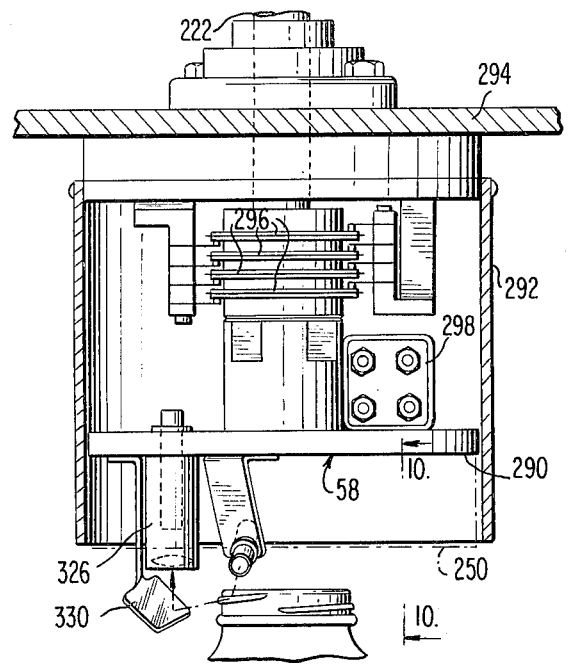
FIG. 9 is a side elevation in partial cross section of the bottle check inspection head.

Turning now to FIG. 9, the inspection head assembly 58 is illustrated in greater detail. The continuously rotating inspection head includes a rotary platform 290 carried at the lower end of the main drive shaft 222. The platform 290 is positioned radially inwardly from a shield 292 which may be directly connected to a ceiling 294 of the inspection tower. Electrical contact between the rotating platform 290 and the ceiling member 294 is established by a plurality of split ring contacts 296. The rotary platform 290 may be provided with a suitable conventional preamplifier 298 to amplify any signal indicating that an imperfect bottle has been inspected.

Figure 12:
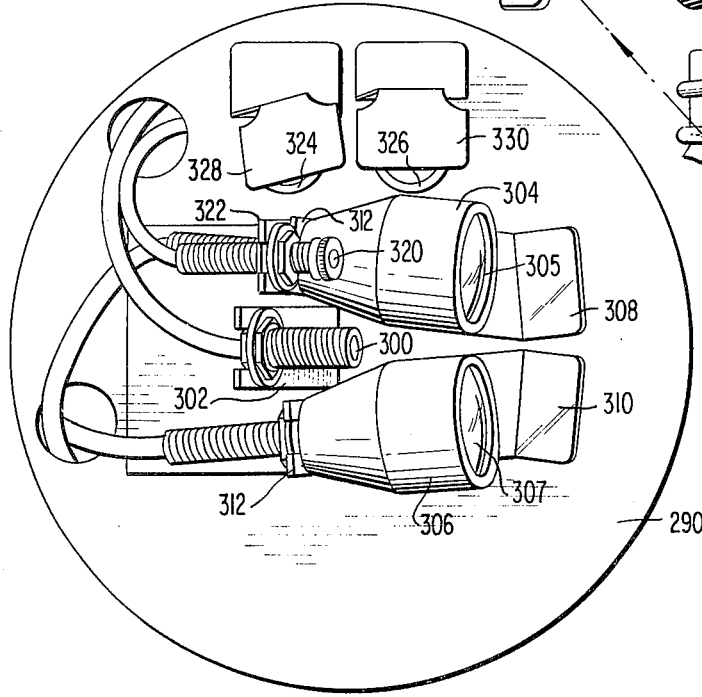
FIG. 12 is a view looking upwardly from the bottom of FIG. 9 to illustrate the relation of the horizontal and vertical check detecting apparatus.

Turning briefly to FIG. 12, the rotary plate 290 is seen to include a first light emitting source 300. Preferably, the source 300 emits radiation in the infrared (IR) wavelength range to reduce possible interference from ambient light. In addition the IR light source 300 generates a pulsed beam. The pulsed beam may operate at a frequency higher than frequencies encountered in the apparatus, e.g.,: 10,000 hertz. The first light source 300 is carried by an inclined plate 302 such that it is inclined downwardly at an angle of approximately 45° and directs light to the rim portion of a bottle from a position near the center of the bottle mouth.

Positioned on each side of the light emitting source 300 is an IR light receiver or collector 304, 306 respectively that generates an electrical pulse when it detects a flash of light. The receivers 304, 306 are coupled to thepulsed frequency of the source 300 to detect light flashes in the proper phase. The light receivers 304, 306 are each provided with a reflecting surface 308, 310 respectively adjacent the forward end. In addition, each receiver 304, 306 includes a double convex focusing lens 305, 307 respectively, that cooperates with the reflecting surfaces 308, 310 to provide a wide detection area.

Figure 11:
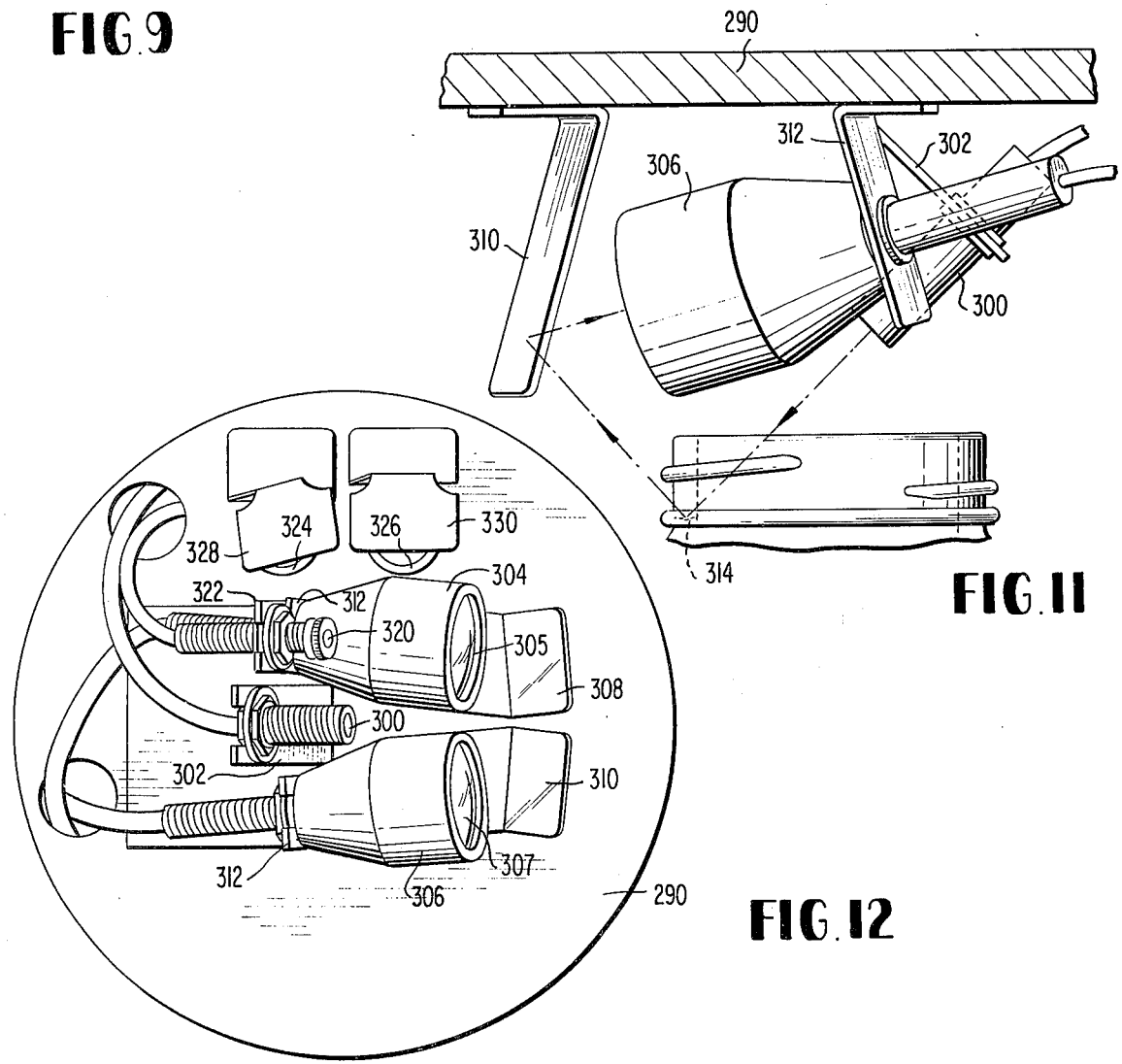
FIG. 11 is an enlarged view of the horizontal check detecting apparatus.

Turning briefly to FIG. 11 it will be noted that the light receivers 306 are generally horizontally oriented with respect to the rotary plate 290 and are carried by downwardly depending supports 312. The first light source 300 and the first pair of light collectors 304, 306 provide apparatus for detecting the presence of generally horizontal cracks, checks, etc. As used herein, generally horizontal it is intended to encompass cracks, checks, etc. having a surface normally disposed at an angle of 45° or less to a horizontal plane.

The reflecting surfaces 308, 310 are suitably connected o the rotary plate 290 and extend downwardly therefrom. However, the reflecting surfaces 308, 310, the light source 300 and the light collectors 304, 306 are all positioned above the plane of the bottle mouth. With continued reference to FIG. 11, light emitted from the source 300 is reflected from an imperfection 314 in the neck portion of a bottle. From the generally horizontal imperfection the light is reflected upwardly to the reflecting surface 310 and then into one of the lenses 305, 307 of the light receiving elements 304, 306. Accordingly, the reflecting surfaces 308, 310 are inclined with respect to one another and inclined with respect to the horizontal rotating platform 290 such that not only horizontal imperfections but imperfections inclined with respect to the horizontal will reflect light upwardly to be received by one of the two light receivers 304, 306. Returning now to FIG. 12 rotary platform 290 is also provided with a second light emitting source 320 which is suitably mounted on a downwardly extending bracket 322. The source 320 is preferably a pulsed IR source. To receive light from the second light source 320 a pair of generally vertical IR light receivers or collectors 324, 326 and reflecting surfaces 328, 330 respectively are provided. The receivers 324, 326 are coupled with the source 320 to detect pulsed IR light. The reflecting surfaces 328, 330 are each carried at the lower end of a finger mounted directly on the platform 290.

The second light emitting source 320 is inclined with respect to the platform 290 at an angle of approximately 30° and directs light toward a neck portion of the bottle from a position above the plane of the bottle mouth and outwardly from the bottle mounth. Each reflecting surface 328, 330 is positioned radially outwardly from the bottle mouth and extends at least partially below the plane of the bottle mouth to receive light reflected from generally vertical cheack, cracks, etc. Generally vertical is intended to encompass checks, cracks, etc. having a surface normal that is inclined more than 45° to a horizontal plane.

Figure 10:
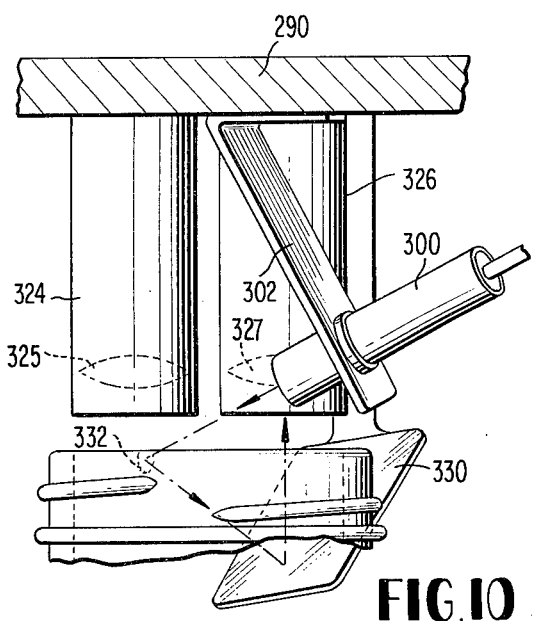
FIG. 10 is an enlarged view of the vertical check detecting apparatus taken along the line 10—10 of FIG. 9.

Turning now to FIG. 10 light emitted from the second light source 300 is reflected by a generally vertically oriented crack, check or imperfection 332 such that it passes downwardly and onto the reflecting surface 330 from which it is reflected generally vertically upwardly into one of the two light receivers 324, 326. The light receivers 324, 326 are provided with a double convex focusing lengs 325, 327, respectively, to increase the field of optical coverage.

To provide the best possible sensitivity to reflected light, the lenses 305, 325, 327 and the reflecting surfaces 308, 310, 328, 330 must be as large as possible. Elementary considerations will indicate that the size of the reflecting surfaces 328, 330 will be critical since the bottle must pass them while they are rotating. The combination of the geneva drive mechanism described above with the continuously rotating inspection head has permitted the reflecting surfaces 328, 330 to be increased.

More specifically, the reflecting surfaces 328, 330 move laterally between the advancing conveyors 78, 78' (see FIG. 5) with a sinusordal motion. The dynamics of the geneva mechanism advancement cooperates with the sinusordal motion of the surfaces 328, 330 to effectively increase the available open space through which the bottle may advance to the inspection position. Accordingly, the reflecting surfaces 328, 330 may be larger that otherwise possible thereby enhancing the optical coverage.

To substantially reduce the potential for inadvertent misalignment of the optical system, the emitters 300, 320, the receivers 304, 306, 324, 326, the reflecting surfaces 308, 310 and the fingers supporting surfaces 328, 330, may be potted in transparent casting material once they are properly aligned. As illustrated in FIG. 9, the casting material 350 may extend from the platform 290 to the lower edge of the skirt 292.

It should now be apparent that the light sources and receivers carried by the rotary plate 290 are effective to detect both generally vertical and generally horizontally oriented cracks, checks and imperfections in the neck portion of a bottle. The output from the first pair of light receivers 304, 306 and the second pair of light receivers 324, 326 may be connected with a preamplifier 298 in order to amplify a sensed imperfection and generate a reject signal for ultimate use in ejecting the imperfect bottle from the supply of bottles. Moreover, it will be apparent to those skilled in the art that the light radiated by the emitters and collected by the receivers is not necessarily limited to the IR spectrum. That is, radiation of any other suitable wavelength might be successfully used as long as the bottle material is trasparent to that wavelength.

In operation, a continuous supply of bottles is conveyed to the inspection station 80 by the supply conveyor 66, the feeding conveyor 70 and the longitudinal conveyor 72. The bottles are guided by the fences 44, 45 and spaced by the rotary screw spacer 74. Spaced bottles are engaged by projecting lugs of intermittently driven advancing assemblies 78 whereupon the bottles are intermittently advanced, one at a time, along the inspection station 80 to the inspection position 82.

To effect bottle advancement, the bottles are alternately pushed forwardly, and then restrained against movement by the longitudinal conveyor 72 by the lugs. Cracks, checks, imperfections and the like are then optically sensed by a continuously rotating sensing head 58 that inspects each bottle twice while it dwells therebelow. The sensing head 58 generates a reject signal which is communicated to a mechanical memory device that mechanically delays relay of the reject signal to a bottle ejecting device 62.

Upon release of the bottle from the inspecting station 80, bottles advance into general alignment with an ejecting device 62. At the same time, the mechanical memory device advances to trigger relay of the reject signal to the ejecting device. Thereupon the ejecting device extends transversely of the longitudinal conveyor 72 and pushes imperfect bottles out of a line of inspected bottles.

The reject signal is communicated to the mechanical memory apparatus 260 (see FIG. 7) by actuation of the solenoid 276. Upon continued rotation of the primary shaft 222, the geneva gear 236 is ultimately advanced, operating the intermittently driven shafts 156, 156' to advance the imperfect bottle forwardly out of the inspection station and into general alignment with the ejecting means 62 (see FIG. 1). With the bottle thus in alignment, the pin 264 (see FIG. 8) engages the limit switch 280 to trigger the solenoid 63 in the ejecting device 62 and reject the bottle laterally from the longitudinal conveyor 72 through the opening 64 in the fence 44 thereof. In the event that the inspection head 58 does not encounter any imperfections in the neck and thread portions of the bottle, no reject signal is generated to the solenoid of the memory apparatus. Accordingly, the bottles passing inspection are permitted to pass forwardly along the longitudinal conveyor 72 to further processing.

While the foregoing description has concerned as apparatus with bottles moving from right to left, the direction of movement is not meant to be a limitation but is for convenience only. For example, apparatus might just as easily be constructed with the bottles moving from left to right.

It should now be apparent that a bottle inspection apparatus constructed in accordance with the present invention has the advantage of eliminating the need for a pair of inspection stations one of which detects horizontal cracks and the second of which detects vertical cracks. Moreover, each bottle at the inspection position is given two complete inspections in the dwell period during which it remains at the inspection position thus effecting a redundant inspection of the bottle.

The bottle advancing assembly is operative to move bottles into and out of the inspection position at a rate which may approximate 120 bottles a minute without interfering with the continuous flow of bottles into the inspection station and without causing damage to any of the bottles.

A further advantage of the present invention is its ability to accommodate bottles of varying capacity and cross-sectional shape by merely changing the lugs appended to the intermittently driven advancing assembly 78.

It should now be apparent that there has been provided in accordance with the present invention a novel bottle check inspection apparatus which substantially satisfies the objects and advantages set forth hereinabove. It will thus be apparent to those skilled in the art that many modifications, variations, substitutions and equivalents may be made for elements of the invention as defined in the appended claims. Accordingly, it is expressly intended that all such modifications, variations, substitutions and equivalents that fall within the spirit and scope of the invention as defined in the appended claims be embraced thereby.

What is claimed is:

1. Apparatus for high speed inspection of a portion of transparent bottles for imperfections comprising:
   an inspection station having an inspection position;
   imperfection sensing means positioned above the inspection position, operable to generate a reject signal when horizontal and vertical imperfections are detected, and operable for continuous rotation;
   conveyor means operable to advance bottles toward the inspection station and to move inspected bottles toward a further processing station;
   intermittent advancing means located at the inspection station, synchronously operable with the sensing means and operable to receive bottles from the conveyor means and intermittently advance bottles one at a time to the inspection position below the sensing means;
   ejection means positioned adjacent to the intermittent advancing means and operable to receive the reject signal and segregate an imperfect bottle fromm perfect bottles;
   wherein the imperfection sensing means includes horizontal detection means for indicating the presence of generally horizontally oriented imperfections having
      first light emitting means directed at a rim portion of a bottle in the inspection position,
      first light collecting means for receiving light reflected upwardly by an imperfection; and
   wherein the imperfection sensing means includes vertical detection means for indicating the presence of generally vertically oriented imperfections having
      second light emitting means directed at a rim portion of a bottle in the inspection position, and
      second light collecting means for receiving light reflected laterally by an imperfection.

2. The apparatus of claim 1 wherein the second light collecting means includes a reflecting surface positioned radially outwardly from the bottle portion inspected, extending below a generally horizontal plane containing the bottle mouth, inclined to reflect light upwardly, and carried by a finger extending downwardly from the sensing means.

3. The apparatus of claim 1 wherein the first light collecting means includes a pair of light receivers positioned on opposite sides of the first light emitter to detect light dispersed by inclined but generally horizontal imperfections.

4. The apparatus of claim 1 wherein the second light collecting means includes:
a pair of light receivers generally vertically positioned in the sensing means; and
a pair of reflecting surfaces, each positioned below a corresponding light receiver, radially outwardly from the bottle portion inspected, extending below a generally horizontal plane containing the bottle mouth, each inclined at a different angle to reflect light upwardly, and carried by a finger extending downwardly from the sensing means.

5. Apparatus for high speed inspection of a portion of transparent bottles for imperfections comprising:
an inspection station having an inspection position;
imperfection sensing means positioned above the inspection position, operable to generate a reject signal when horizontal and vertical imperfections are detected, and operable for continuous rotation;
conveyor means operable to advance bottles toward the inspection station and to move inspected bottles toward a further processing station;
intermittent advancing means located at the inspection station,ng synchronously operable with the sensing means and operable to receive bottles from the conveyor means and intermittently advance bottles one at a time to the inspection position below the sensing means;
ejection means positioned adjacent to the intermittent advancing means and operable to receive the reject signal and segregate an imperfect bottle from perfect bottles; and
wherein the intermittent advancing means includes a pair of endless conveyors, each positioned on opposite sides of the inspection station, defining a bottle receiving space therebetween, and driven such that each endless conveyor advances in the same direction through the bottle receiving space, and engaging means carried by each endless conveyor, projecting outwardly therefrom to define opposed pairs throughout the bottle receiving space, cooperating to detain bottles from advancement by the conveyor means to advance bottles one at a time to the inspection position located in the bottle receiving space.

6. The apparatus of claim 5 wherein the engaging means includes one of a first set of lugs for half gallon size bottles, a second set of lugs for round quart size bottles, and a third set of lugs for square quart size bottles.

7. The apparatus of claim 5 further including a mechanical memory means for mechanically delaying communication of the reject signal to the ejection means until an imperfect bottle is generally aligned therewith.

8. The apparatus of claim 7 wherein the mechanical memory means includes:
a rotatable plate having an axis and a plurality of circumferentially spaced axially extending openings therethrough;
a corresponding plurality of elongate pins, each pin being slidably received in a corresponding opening of the plate;
a reset means spaced from a first side of the plate in general alignment with the locus of the plurality of openings and operable to reset each of the pins to a position extending from the second side of the plate;
setting means spaced from the second side of the plate in general axial alignment with the pins and operable to slide a pin to a position extending from the first side of the plate upon receipt of a reject signal; and
pickoff means arcuately spaced between the setting means and the reset means such that the plate rotates from the actuator means to the pickoff means to the reset means and operable to be engaged by any pin extending from the first side of the plate to generate a continuation of the reject signal.

9. The apparatus of claim 8 wherein the pickoff means comprises a limit switch.

10. The apparatus of claim 8 wherein the plate is carried by and synchronously intermittently advanced by the advancing means.

11. Apparatus for high speed inspection of a portion of transparent bottles for imperfections comprising:
an inspection station having an inspection position;
imperfections sensing means positioned above the inspection position, operable to generate a reject signal when horizontal and vertical imperfections are detected, and operable for continuous rotation;
conveyor means operable to advance bottles toward the inspection station and to move inspected bottles toward a further processing station;
intermittent advancing means located at the inspection station, synchronously operable with the sensing means and operable to receive bottles from the conveyor means and intermittently advance bottles one at a time to the inspection position below the sensing means;
ejection means positioned adjacent to the intermittent advancing means and operable to receive the reject signal and segregate and imperfect bottle from perfect bottles;
geneva gear means having an input gear, drivingly connected to the intermittent advancing means and operable to convert continuous rotary motion into intermittent rotary motion; and
means for synchronously driving both the geneva gear means input gear and the sensing means.

12. The apparatus of claim 11 wherein the sensing means is rotatable at four times the angular velocity of the input gear so that the sensing means may perform two inspections of each bottle.

13. The apparatus of claim 11 wherein a variable speed motor drives the gear means to effect a variable rate of bottle inspection.

14. A method of rapidly inspecting transparent bottles including the steps of:
conveying a plurality of transparent bottles on a linear conveyor toward an inspection station;
intermittently advancing bottles one at a time from the linear conveyor into an inspection position;
sensing the presence of generally horizontal and generally vertical imperfections in a bottle with a sensor head located at the inspection position;

generating a reject signal from the sensor head when a generally horizontal or a generally vertical imperfection is sensed;

releasing the inspected bottle onto a conveyor for subsequent movement;

segregating imperfect bottles and perfect bottles at a location spaced from the inspection station in response to the reject signal; and wherein the step of intermittently advancing includes restraining the bottles from movement by the linear conveyor by engagement between opposed intermittently advancing assemblies, and pushing the bottles forwardly toward the inspection position with spacers extending in opposed relation from the advancing assemblies.

15. The method of claim 14 wherein the sensing step includes:

continuously rotating the sensor head above the inspection station; and inspecting the bottle by revolving the sensor head through at least two complete revolutions before the releasing step.

16. The method of claim 14 wherein the segregating step includes the step of pushing imperfect bottles out of an advancing line of inspected bottles.

17. The method of claim 16 wherein the pushing step includes:

mechanically delaying the reject signal until the imperfect bottle is generally aligned with a reject assembly; and actuating a solenoid of the reject assembly in response to the delayed reject signal to exclude the imperfect bottle from the advancing line of inspected bottles.

18. In bottle inspection apparatus of the type having a continuously rotatably optical inspection head and means for advancing bottles to and detaining bottles at an inspection station, and improved driving means for relating bottle advancement and inspection head position comprising:

geneva gear means having a driving gear operatively connected to the rotatable inspection head and a driven gear operatively connected to the advancing means and being operable to transform rotary motion of the driven gear into intermittent advancing motions spaced by dwell periods.

19. The apparatus of claim 18 wherein the rotatable inspection head makes two complete revolutions during each dwell period to inspect a bottle positioned at the inspection position.

20. In a bottle inspection device of the type having a rotatable inspection head and means for advancing bottles to an inspection position below the inspection head, an improved inspection head for sensing both vertical and horizontal imperfections comprising:

a first light emitter attached to the bottom of the inspection head positioned to direct light downwardly toward a neck portion of the bottle from a location centrally of the bottle;

a first pair of light receivng means attached to the bottom of the inspection head, each disposed to one side of the first emitter and operable to receive specular reflections from generally horizontal imperfections;

a second light emitter attached to the bottom of the inspection head, positioned to direct light downwardly toward the neck portion from a location centrally of the bottle; and a second pair of light receiving means attached to the bottom of the inspection head, each disposed to receive specular reflections from generally vertical imperfections illuminated by the second emitter.

21. The apparatus of claim 20 wherein each of the first pair of receiving means includes a generally horizontally mounted light receiver and a reflecting surface positioned outwardly from the bottle mouth and inclined to direct specularly reflected light into the corresponding light receiver.

22. The apparatus of claim 20 wherein each of the second pair of receiving includes a generally vertically mounted light receiver and a reflecting surface carried on a finger extending from the head to a position below the plane defined by the bottle mouth, each reflecting surface being inclined to direct specularly reflected light into one of the light receivers.

* * * * *